(12) United States Patent
Peglion et al.

(10) Patent No.: US 8,119,794 B2
(45) Date of Patent: Feb. 21, 2012

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Aimee Dessinges, Rueil Malmaison (FR); Bernard Serkiz, Servon Brie Comte Robert (FR)

(73) Assignee: Les Laboratoires Servier, Suresnes Cedex (FR)

( * ) Notice: Subject to any disclaimer, the term of this patent is extended or adjusted under 35 U.S.C. 154(b) by 194 days.

(21) Appl. No.: 12/798,048

(22) Filed: Mar. 29, 2010

(65) Prior Publication Data

US 2010/0249398 A1     Sep. 30, 2010

(30) Foreign Application Priority Data

Mar. 31, 2009   (FR) ...................................... 09 01556

(51) Int. Cl.
*C07D 223/18*   (2006.01)
(52) U.S. Cl. ..................................................... 540/523
(58) Field of Classification Search .................... 540/523
See application file for complete search history.

(56) References Cited

FOREIGN PATENT DOCUMENTS

| EP | 0534859 | 3/1993 |
|---|---|---|
| EP | 1598333 | 11/2005 |
| WO | WO 2005/110993 | 11/2005 |

OTHER PUBLICATIONS

Bomhard A., et al., "Specific bradycardic agents. 2. heteroaromatic modifications in the side chain of specific bradycardic benzazepinones . . . " Journal of Medicinal Chemistry, vol. 34, p. 942-947, Jan. 1, 1991.
French Preliminary Search Report for FR0901556 of Aug. 31, 2009.
Rousselet, et al., Copper(I)-induced addition of amines to unactivatied nitriles: The first general one-step synthesis of alkyl amidines: Tetrahedron Letters, vol. 34, No. 40, pp. 6395-6398, Oct. 1, 1993.

*Primary Examiner* — Bruck Kifle
(74) *Attorney, Agent, or Firm* — Hueschen and Sage

(57) ABSTRACT

Process for the synthesis of ivabradine of formula (I):

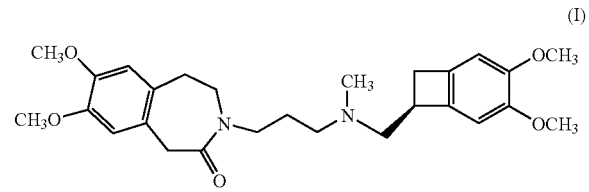

(I)

and addition salts thereof with a pharmaceutically acceptable acid.

7 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

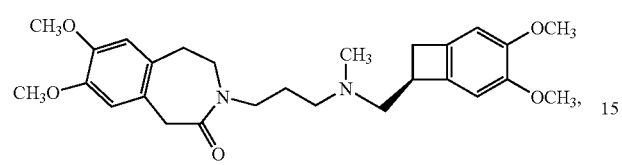

(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine hydrochloride starting from the compound of formula (II):

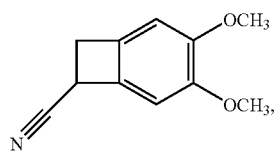

(II)

which is subjected to a reduction reaction to yield the compound of formula (III):

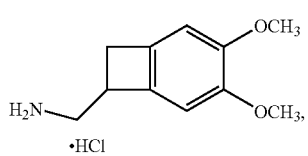

(III)

which is converted into the compound of formula (IV):

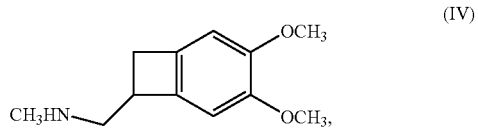

(IV)

which is resolved to yield the compound of formula (V):

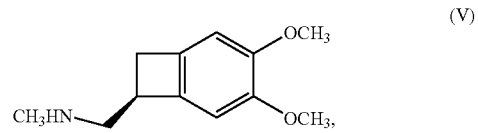

(V)

which is reacted with the compound of formula (VI):

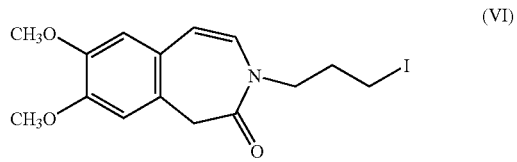

(VI)

to yield the compound of formula (VII):

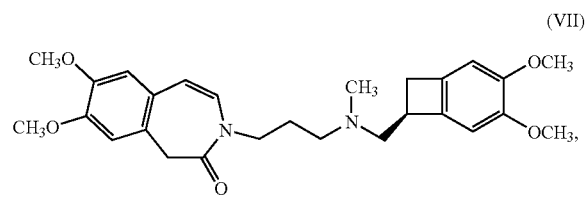

(VII)

the catalytic hydrogenation of which yields ivabradine, which is then converted into its hydrochloride.

The disadvantage of that synthesis route is that it results in ivabradine in a yield of the order of only 0.5%.

In view of the pharmaceutical value of this compound, it has been important to be able to obtain it by an effective synthesis process resulting in ivabradine in a good yield.

The present invention relates to a process for the synthesis of the compound of formula (VIII), in racemic or optically active form:

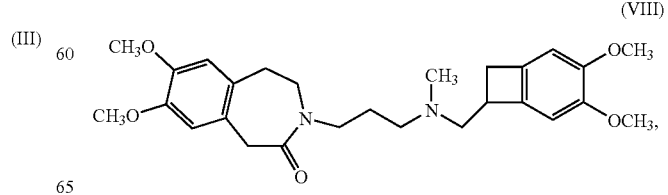

(VIII)

characterised in that the compound of formula (II), in racemic or optically active form:

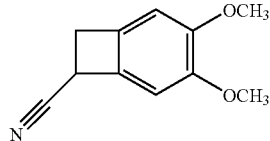
(II)

is reacted with the compound of formula (IX):

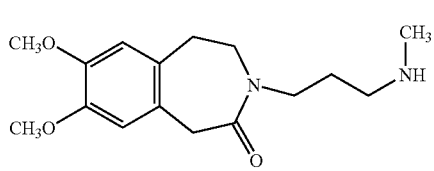
(IX)

in the presence of a salt of a transition metal or of a lanthanide, in a solvent,
to yield the compound of formula (X), in racemic or optically active form:

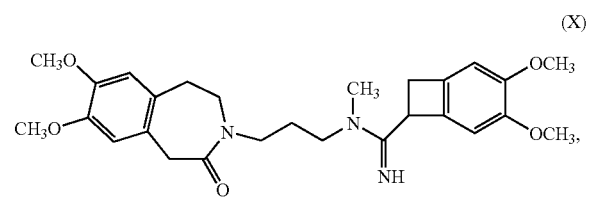
(X)

which is converted into the compound of formula (VIII) by the action of a hydride donor agent.

In a preferred embodiment of the invention, the compound of formula (II) is in optically active form, more especially of configuration (S). The product of the reaction of the compound of formula (X) with the hydride donor agent is then ivabradine of formula (I), a particular case of the compounds of formula (VIII):

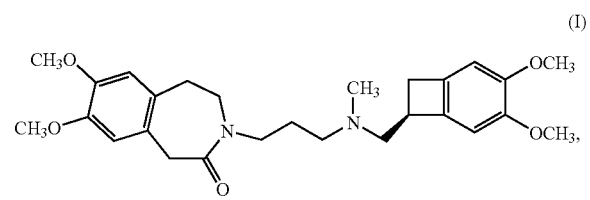
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

In another preferred embodiment of the invention, the compound of formula (II) is in racemic form. The reaction of the compound of formula (X) with a hydride donor agent is then followed by a step of optical resolution of the compound of formula (VIII) obtained in racemic form, to yield ivabradine of formula (I):

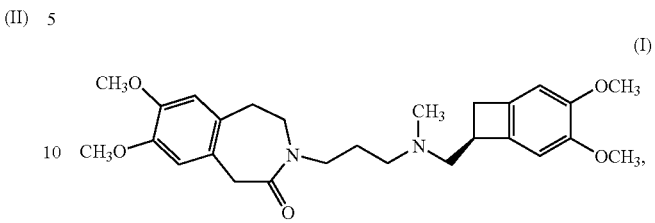
(I)

which may optionally be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Among the salts of transition metals or of lanthanides that may be used to carry out the reaction between the compound of formula (II) and the compound of formula (IX), there may be mentioned, without implying any limitation, copper(I) chloride, copper(I) bromide, copper(I) iodide, yttrium(III) trifluoromethanesulphonate, lanthanum(III) trifluoromethanesulphonate, praseodymium(III) trifluoromethanesulphonate, neodymium(III) trifluoromethanesulphonate, samarium(III) trifluoromethanesulphonate, europium(III) trifluoromethanesulphonate, gadolinium(III) trifluoromethanesulphonate, terbium(III) trifluoromethanesulphonate, dysprosium(III) trifluoromethanesulphonate, holmium (III) trifluoromethanesulphonate, erbium(III) trifluoromethanesulphonate and lutetium(III) trifluoromethanesulphonate.

Preference is given to the transition metal salt used for carrying out the reaction between the compound of formula (II) and the compound of formula (IX) being copper(I) chloride. Among the solvents that may be used for carrying out the reaction between the compound of formula (II) and the compound of formula (IX) there may be mentioned, without implying any limitation:
  alcoholic solvents, especially methanol, ethanol and isopropanol;
  dimethyl sulphoxide (DMSO);
  N,N-dimethylformamide (DMF);
  N-methylpyrrolidone (NMP).

Preference is given to the solvent used for carrying out the reaction between the compound of formula (II) and the compound of formula (IX) being methanol.

Among the hydride donor agents that may be used for carrying out the conversion of the compound of formula (X) into the compound of formula (VIII) there may be mentioned, without implying any limitation, sodium tetraborohydride, sodium cyanoborohydride and also the complexes borane-morpholine and borane-dimethylamine.

Preference is given to the hydride donor agent used for carrying out the conversion of the compound of formula (X) into the compound of formula (VIII) being sodium tetraborohydride.

Among the solvents that may be used for carrying out the conversion of the compound of formula (X) into the compound of formula (VIII) there may be mentioned, without implying any limitation:

alcoholic solvents, especially methanol, ethanol and isopropanol;
N,N-dimethylformamide (DMF);
N-methylpyrrolidone (NMP).

The compounds of formula (X), in racemic or optically active form, are new products which are useful as synthesis intermediates in the chemical or pharmaceutical industry, especially in the synthesis of ivabradine, addition salts thereof with a pharmaceutically acceptable acid and hydrates thereof, and as such they form an integral part of the present invention. The Examples hereinbelow illustrate the invention.
List of abbreviations used:
IR: infra-red

EXAMPLE 1

3-{3-[[(3,4-dimethoxybicyclo[4.2.0]octa-1,3,5-trien-7-yl)methyl]-(methyl)amino]propyl}-7,8-dimethoxy-1,3,4,5-tetrahydro-2H-3-benzazepin-2-one Step 1: N-[3-(7,8-dimethoxy-2-oxo-1,2,4,5-tetrahydro-3H-3-benzazepin-3-yl)propyl]-3,4-dimethoxy-N-methylbicyclo[4.2.0]octa-1,3,5-triene-7-carboximidamide Under nitrogen, 2 g (10.6 mmol) of 3,4-dimethoxybicyclo[4.2.0]octa-1,3,5-triene-7-carbonitrile are dissolved in 10 mL of methanol. To the resulting solution there are added 1.3 g (12.7 mmol, 1.2 equivalents) of copper(I) chloride (purity 99%). Then 4.6 g (15.9 mmol, 1.5 equivalents) of 7,8-dimethoxy-3-[3-(methylamino)propyl]-1,3,4,5-tetra-hydro-2H-3-benzazepin-2-one dissolved in 20 mL of methanol are added dropwise. Heating at reflux is carried out for 24 hours. Cooling to 0° C. is carried out, concentrated hydrochloric acid is added until the pH is 2 and stirring is carried out for 10 minutes in order to decomplex the copper salts. The pH is then brought to 8 by adding 20% aqueous sodium hydroxide solution. The aqueous phase is extracted with dichloromethane, dried over MgSO$_4$, filtered and then evaporated to dryness. There are obtained 6.4 g of a brown oil containing 35% expected product in admixture with 21% starting amine. This oil is used without purification in the step that follows.

Step 2: 3-{3-[[(3,4-dimethoxybicyclo[4.2.0]octa-1,3,5-trien-7-yl)methyl]methyl)amino]-propyl}-7,8-dimethoxy-1,3,4,5-tetrahydro-2H-3-benzazepin-2-one 6.4 g of the product obtained in Step 1 are dissolved in 65 mL of methanol. 481 mg (12.7 mmol, 1.2 equivalents) of sodium tetraborohydride are then added at 25° C. Stirring is carried out overnight at ambient temperature. 26 mL of 20% aqueous sodium hydroxide solution and 100 mL of dichloromethane are added and vigorous stirring is carried out for 15 minutes. The organic phase is washed with water, dried over MgSO$_4$, filtered and then evaporated to dryness. There are obtained 6.6 g of an oil which is purified by flash chromatography on 300 g of silica (eluant=dichloromethane/ethanol/NH$_4$OH: 90/10/1). There are obtained 1.6 g of the title product in the form of an oil, which crystallises at ambient temperature.
Yield=33% (over 2 steps)
IR (pure): ν=1633, 831, 672 cm$^{-1}$.

EXAMPLE 2

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride 2.1 g of the racemic compound obtained in the Example above are separated on a 60 cm×60 mm column packed with 2.1 kg of Chiralpak® AD phase (particle size 20 μm). The eluant used is a mixture of ethanol/acetonitrile/diethylamine (10/90/0.1 by volume) at a flow rate of 50 mL/min. The associated ultra-violet detector is used at a wavelength of 280 nm.

There are obtained 0.95 g of the enantiomer of configuration (R) in the form of a white meringue and then 0.95 g of the enantiomer of configuration (S), also in the form of a white meringue.

The hydrochloride of the enantiomer of configuration (S) is then obtained by following the procedure described in patent specification EP 0 534 859 (Example 2, Step E).

The invention claimed is:
1. A process for the synthesis of the compound of formula (VIII), in racemic or optically active form:

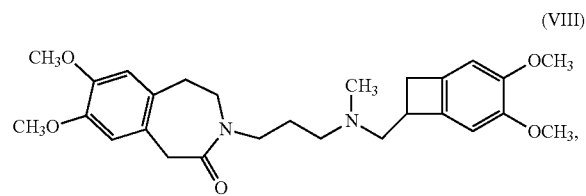

(VIII)

wherein a compound of formula (II), in racemic or optically active form:

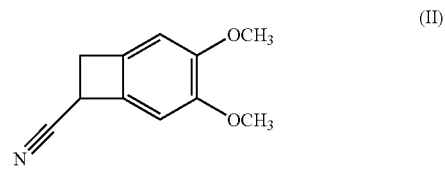

(II)

is reacted with a compound of formula (IX):

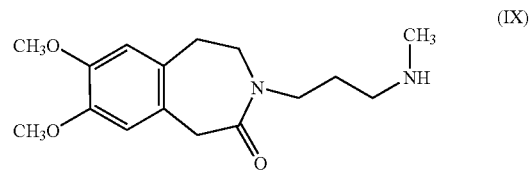

(IX)

in the presence of a salt of a transition metal or of a lanthanide,
in a solvent,
to yield a compound of formula (X), in racemic or optically active form:

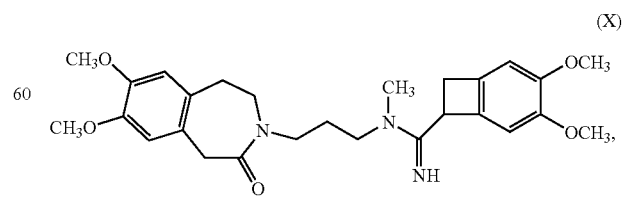

(X)

which is converted into the compound of formula (VIII) by the action of a hydride donor agent.

2. The process of claim 1, wherein the compound of formula (II) is of configuration (S), and wherein the product of the reaction of the compound of formula (X) with the hydride donor agent is ivabradine of formula (I):

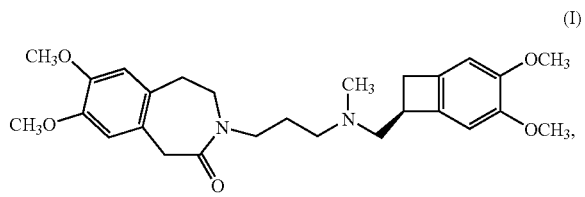

which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

3. The process of claim 1, wherein the compound of formula (II) is in racemic form, and wherein the reaction of the compound of formula (X) with the hydride donor agent is followed by a step of optical resolution of the compound of formula (VIII) obtained in racemic form, to yield ivabradine of formula (I):

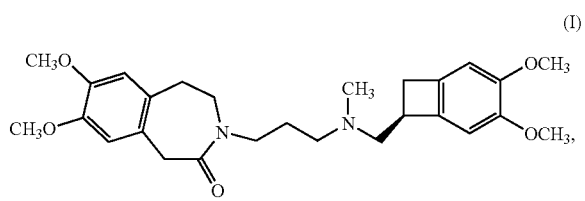

which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into a hydrate thereof.

4. The process of claim 1, wherein the salt of a transition metal or of a lanthanide used to carry out the reaction between the compound of formula (II) and the compound of formula (IX) is selected from copper(I) chloride, copper(I) bromide, copper(I) iodide, yttrium(III) trifluoromethanesulphonate, lanthanum(III) trifluoromethanesulphonate, praseodymium(III) trifluoromethanesulphonate, neodymium(III) trifluoromethanesulphonate, samarium(III) trifluoromethanesulphonate, europium(III) trifluoromethanesulphonate, gadolinium(III) trifluoromethanesulphonate, terbium(III) trifluoromethanesulphonate, dysprosium(III) trifluoromethanesulphonate, holmium(III) trifluoromethanesulphonate, erbium(III) trifluoromethanesulphonate and lutetium(III) trifluoromethanesulphonate.

5. The process of claim 1, wherein the solvent used to carry out the reaction between the compound of formula (II) and the compound of formula (IX) is selected from alcoholic solvents, dimethyl sulphoxide, N,N-dimethylformamide and N-methylpyrrolidone.

6. The process of claim 1, wherein the hydride donor agent used to carry out the conversion of the compound of formula (X) to the compound of formula (VIII) is selected from sodium tetraborohydride, sodium cyanoborohydride, the complex borane-morpholine and the complex borane-dimethylamine.

7. A compound of formula (X), in racemic or optically active form:

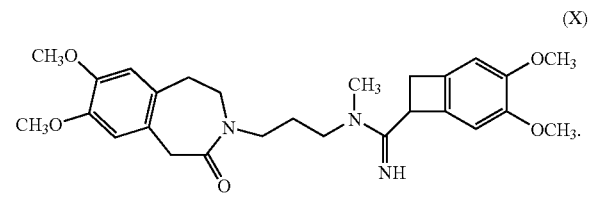

* * * * *